United States Patent
Trieu

(10) Patent No.: US 6,974,479 B2
(45) Date of Patent: Dec. 13, 2005

(54) SYSTEM AND METHOD FOR BLOCKING AND/OR RETAINING A PROSTHETIC SPINAL IMPLANT

(75) Inventor: Hai H. Trieu, Cordova, TN (US)

(73) Assignee: SDGI Holdings, Inc., Wilmington, DE (US)

( * ) Notice: Subject to any disclaimer, the term of this patent is extended or adjusted under 35 U.S.C. 154(b) by 0 days.

(21) Appl. No.: 10/419,364

(22) Filed: Apr. 21, 2003

(65) Prior Publication Data

US 2004/0111161 A1 Jun. 10, 2004

Related U.S. Application Data

(60) Provisional application No. 60/432,368, filed on Dec. 10, 2002.

(51) Int. Cl.$^7$ ................................................ A61F 2/44
(52) U.S. Cl. ..................................... 623/17.11; 606/61
(58) Field of Search ......................... 623/17.11, 17.12, 623/17.13, 17.14, 17.15, 17.16; 606/61

(56) References Cited

U.S. PATENT DOCUMENTS

| | | |
|---|---|---|
| 3,867,728 A | 2/1975 | Stubstad et al. |
| 3,875,595 A | 4/1975 | Froning |
| 4,309,777 A | 1/1982 | Patil |
| 4,349,921 A | 9/1982 | Kuntz |
| 4,759,766 A | 7/1988 | Beuttner-Jantz et al. |
| 4,759,769 A | 7/1988 | Hedman et al. |
| 4,772,287 A | 9/1988 | Ray et al. |
| 4,863,477 A | 9/1989 | Monson |
| 4,874,389 A | 10/1989 | Downey |
| 4,904,260 A | 2/1990 | Ray et al. |
| 4,911,718 A | 3/1990 | Lee et al. |
| 4,917,704 A | 4/1990 | Frey et al. |
| 4,932,969 A | 6/1990 | Frey et al. |
| 4,946,378 A | 8/1990 | Hirayama et al. |
| 4,955,908 A | 9/1990 | Frey et al. |
| 4,997,432 A | 3/1991 | Keller |
| 5,002,576 A | 3/1991 | Fuhrmann et al. |
| 5,035,716 A | 7/1991 | Downey |
| 5,047,055 A | 9/1991 | Bao et al. |
| 5,071,437 A | 12/1991 | Steffee |
| 5,108,438 A | 4/1992 | Stone |
| 5,171,280 A | 12/1992 | Baumgartner |
| 5,192,326 A | 3/1993 | Bao et al. |
| 5,306,307 A | 4/1994 | Senter et al. |
| 5,306,308 A | 4/1994 | Gross et al. |
| 5,370,697 A | 12/1994 | Baumgartner |
| 5,401,269 A | 3/1995 | Buttner-Jantz et al. |
| 5,423,816 A | 6/1995 | Lin |
| 5,425,773 A | 6/1995 | Boyd et al. |
| 5,458,643 A | 10/1995 | Oka et al. |
| 5,507,816 A | 4/1996 | Bullivant |

(Continued)

FOREIGN PATENT DOCUMENTS

EP  0 700 671 A1  3/1996

(Continued)

*Primary Examiner*—Bruce E. Snow
(74) *Attorney, Agent, or Firm*—Woodard, Emhardt, Moriarty, McNett & Henry LLP

(57) ABSTRACT

Devices for anchoring and/or blocking spinal implants in an intervertebral disc space are disclosed. In one aspect of the invention the device includes a rigid blocking member having one end unconnected and free to block a spinal implant, and another end attached to a securing member to secure the blocking member to the spine. Methods for using the inventive anchoring/blocking implants are also provided.

19 Claims, 11 Drawing Sheets

U.S. PATENT DOCUMENTS

| | | |
|---|---|---|
| 5,534,028 A | 7/1996 | Bao et al. |
| 5,534,030 A | 7/1996 | Navarro et al. |
| 5,545,229 A | 8/1996 | Parsons et al. |
| 5,549,679 A | 8/1996 | Kuslich |
| 5,556,431 A | 9/1996 | Buttner-Janz |
| 5,562,738 A | 10/1996 | Boyd et al. |
| 5,571,189 A | 11/1996 | Kuslich |
| 5,645,597 A | 7/1997 | Krapiva |
| 5,674,294 A | 10/1997 | Bainville et al. |
| 5,674,295 A | 10/1997 | Ray et al. |
| 5,674,296 A | 10/1997 | Bryan et al. |
| 5,683,464 A | 11/1997 | Wagner et al. |
| 5,683,465 A | 11/1997 | Shinn et al. |
| 5,693,100 A | 12/1997 | Pisharodi |
| 5,702,450 A | 12/1997 | Bisserie |
| 5,716,416 A | 2/1998 | Lin |
| 5,755,796 A | 5/1998 | Ibo et al. |
| 5,755,797 A | 5/1998 | Baumgartner |
| 5,824,093 A | 10/1998 | Ray et al. |
| 5,824,094 A | 10/1998 | Serhan et al. |
| 5,827,328 A | 10/1998 | Buttermann |
| 5,888,226 A | 3/1999 | Rogozinski |
| 5,893,889 A | 4/1999 | Harrington |
| 5,895,428 A | 4/1999 | Berry |
| 5,976,186 A | 11/1999 | Bao et al. |
| 6,001,130 A | 12/1999 | Bryan et al. |
| 6,093,205 A | 7/2000 | McLeod et al. |
| 6,120,503 A | 9/2000 | Michelson |
| 2002/0120270 A1 | 8/2002 | Trieu et al. |
| 2003/0078579 A1 * | 4/2003 | Ferree ................... 606/53 |
| 2003/0120274 A1 | 6/2003 | Morris et al. |
| 2003/0195514 A1 * | 10/2003 | Trieu et al. ............. 606/61 |

FOREIGN PATENT DOCUMENTS

| | | |
|---|---|---|
| FR | 9713056/2769827 | 10/1997 |
| WO | WO 90/11740 | 10/1990 |
| WO | WO 95/31946 | 11/1995 |
| WO | WO 96/01598 | 1/1996 |
| WO | WO 97/26847 | 7/1997 |
| WO | WO 97/37620 | 10/1997 |
| WO | WO 98/04217 | 2/1998 |
| WO | WO 02/17824 A2 | 3/2002 |
| WO | WO02/17825 | 3/2002 |
| WO | WO02/45592 | 6/2002 |
| WO | WO02/058599 | 8/2002 |

* cited by examiner

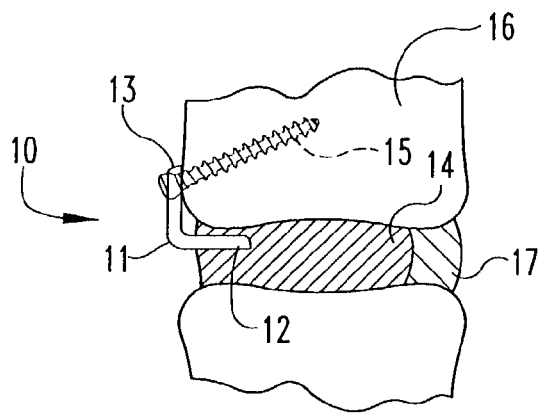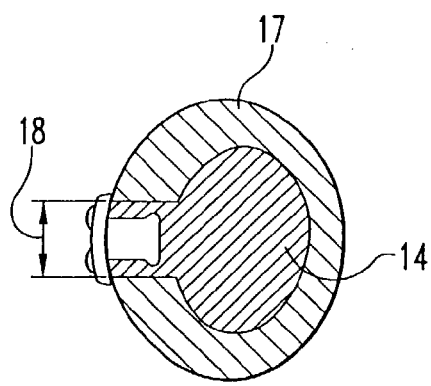
Fig. 1a      Fig. 1b
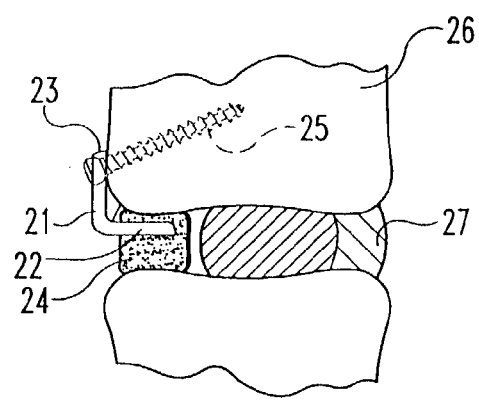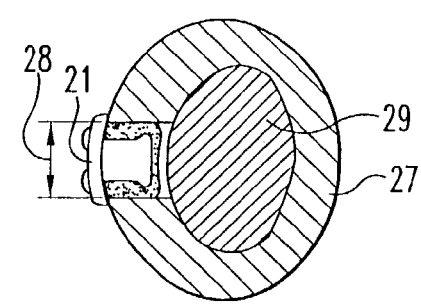
Fig. 2a      Fig. 2b
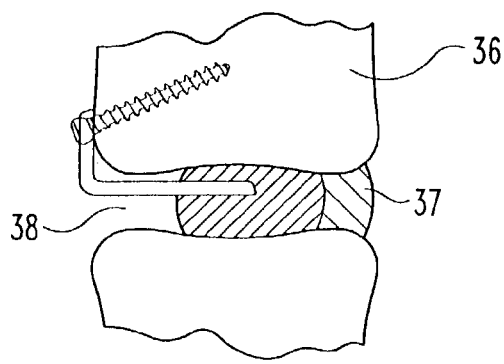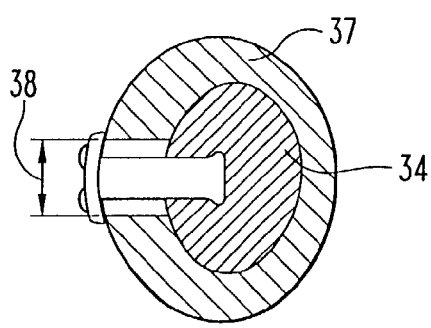
Fig. 3a      Fig. 3b

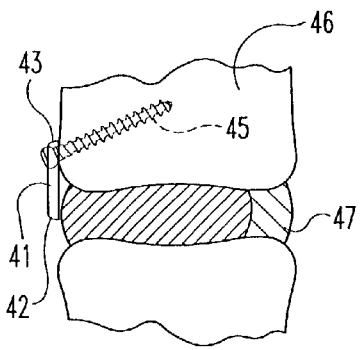
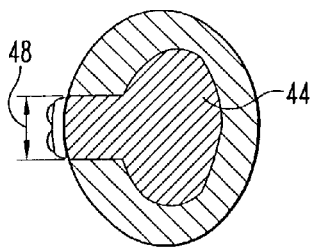
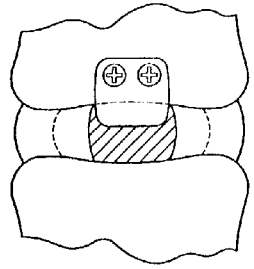
Fig. 4a  Fig. 4b  Fig. 4c
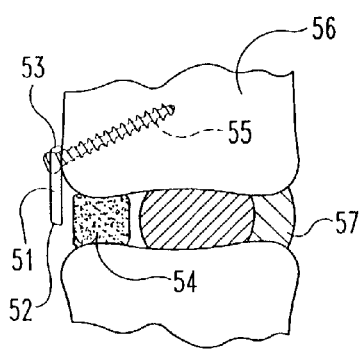
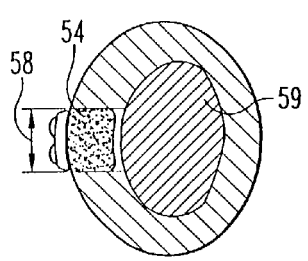
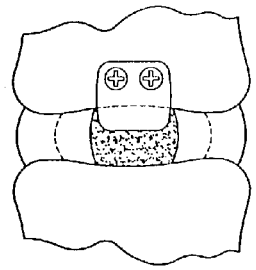
Fig. 5a  Fig. 5b  Fig. 5c
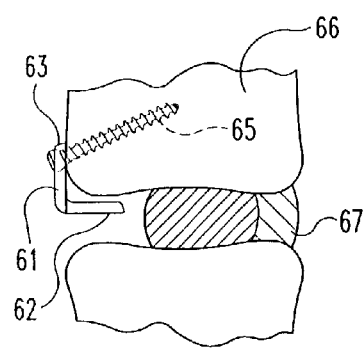
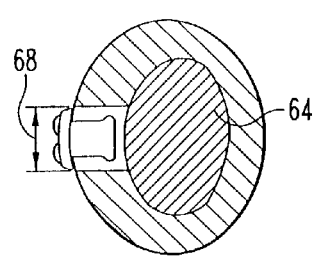
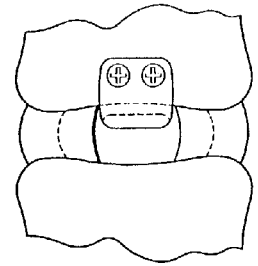
Fig. 6a  Fig. 6b  Fig. 6c

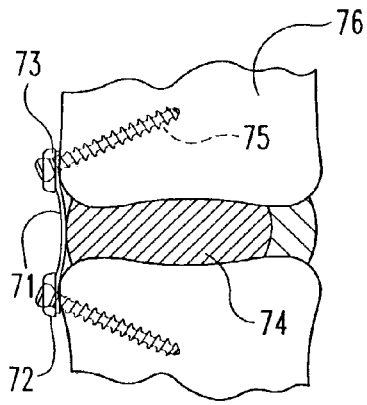 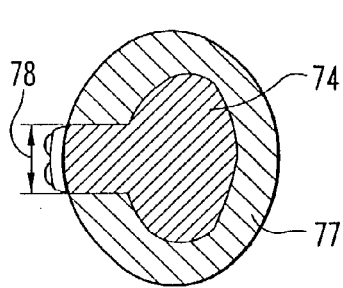 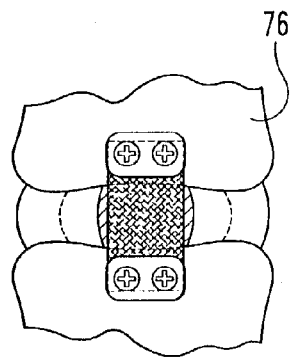
Fig. 7a　　Fig. 7b　　Fig. 7c
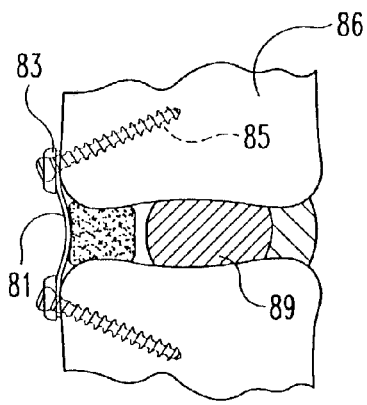 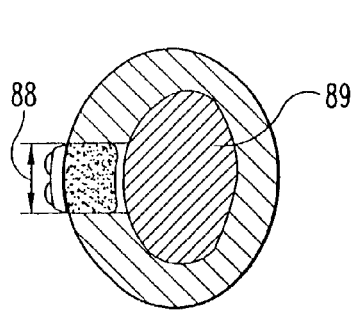 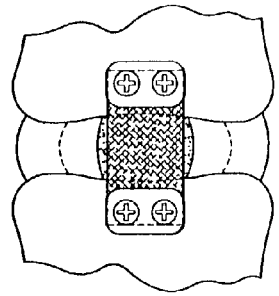
Fig. 8a　　Fig. 8b　　Fig. 8c
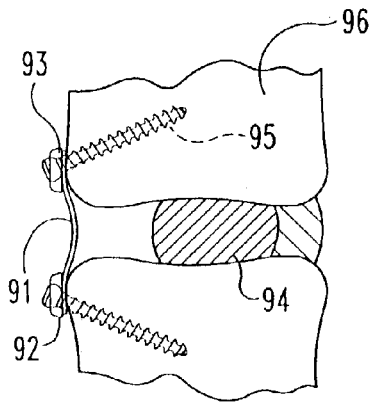 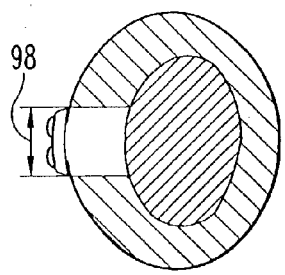 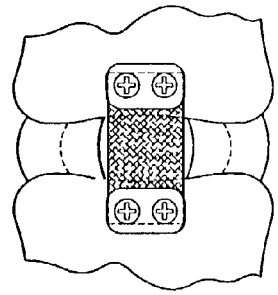
Fig. 9a　　Fig. 9b　　Fig. 9c

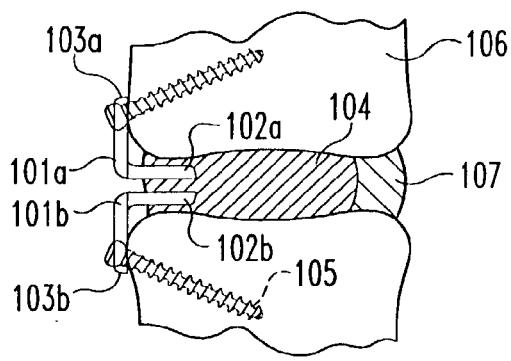 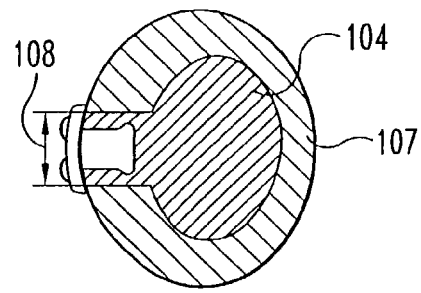
Fig. 10a  Fig. 10b
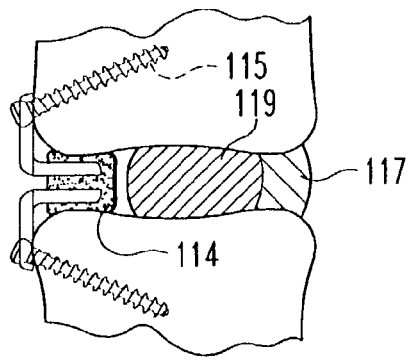 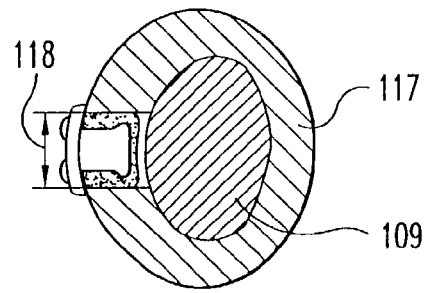
Fig. 11a  Fig. 11b
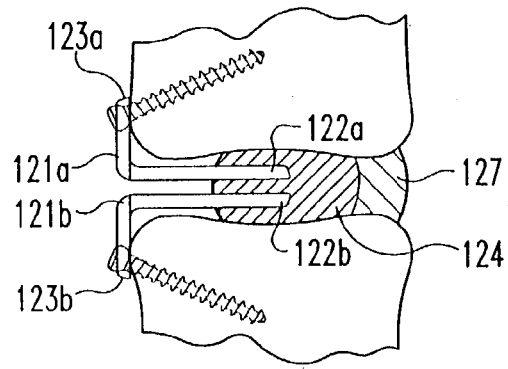 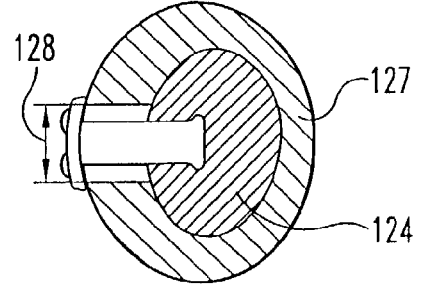
Fig. 12a  Fig. 12b

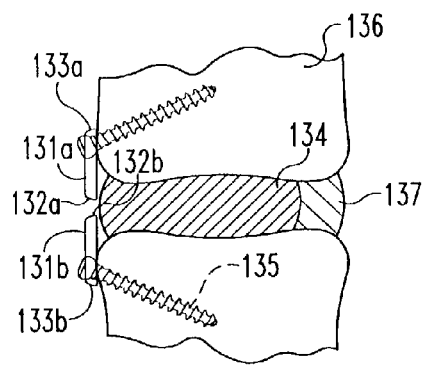
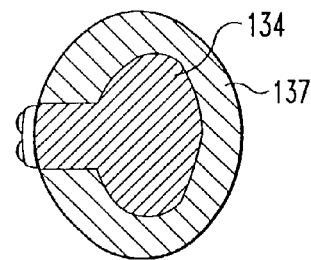
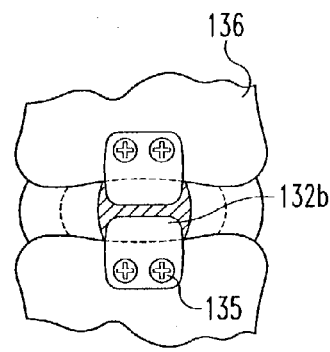
Fig. 13a     Fig. 13b     Fig. 13c
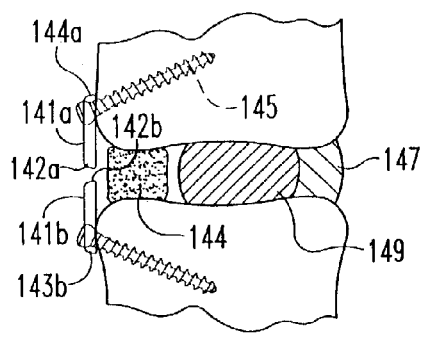
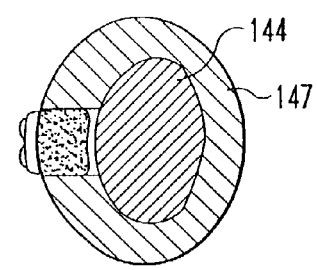
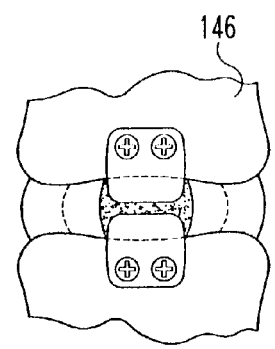
Fig. 14a     Fig. 14b     Fig. 14c
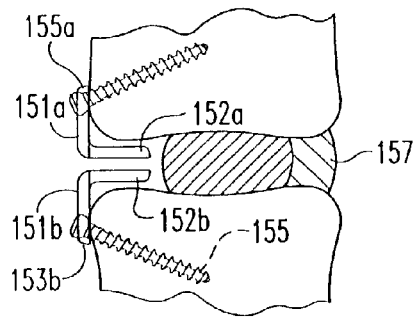
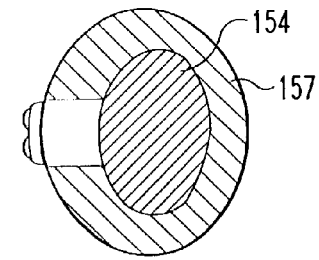
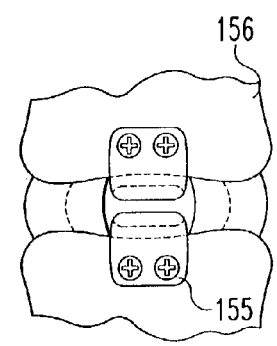
Fig. 15a     Fig. 15b     Fig. 15c

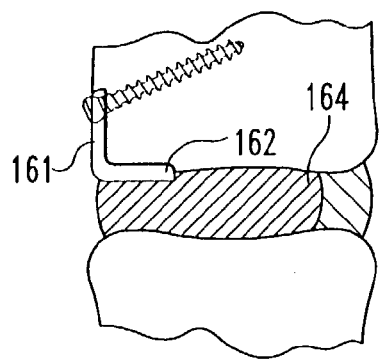 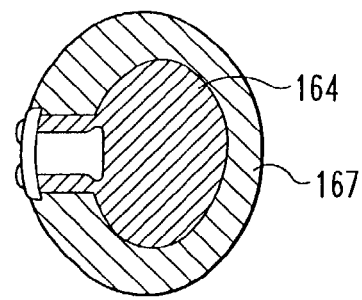
Fig. 16a  Fig. 16b
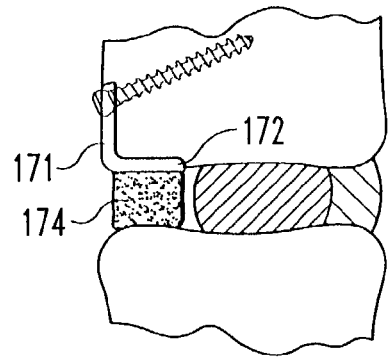 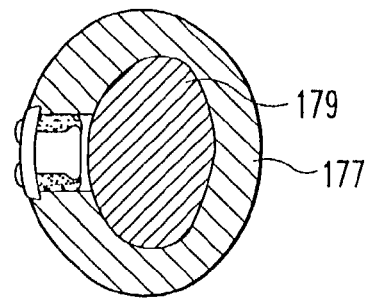
Fig. 17a  Fig. 17b
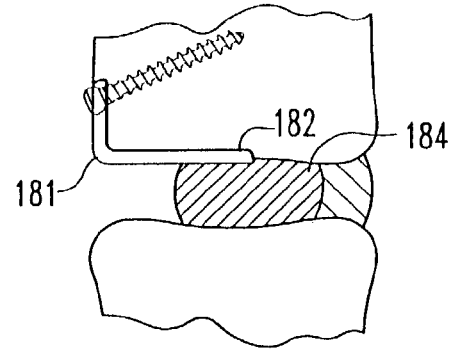 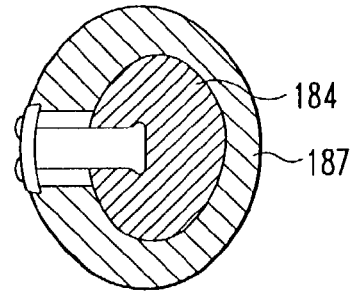
Fig. 18a  Fig. 18b

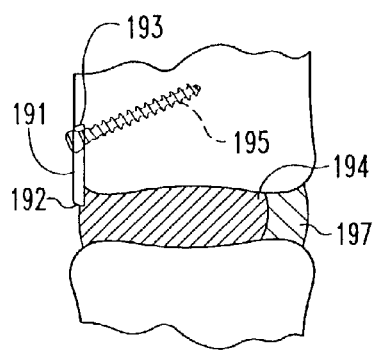 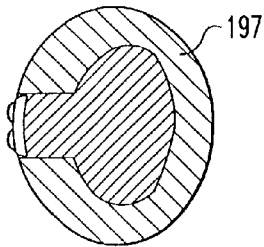 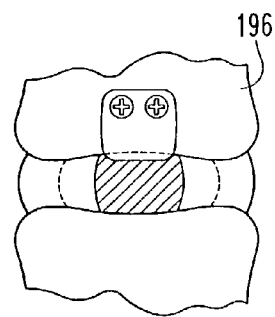
Fig. 19a   Fig. 19b   Fig. 19c
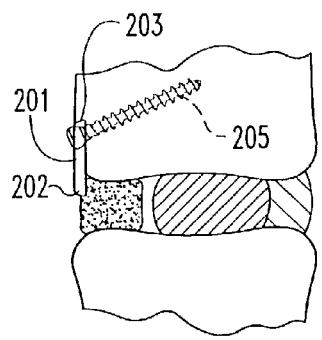 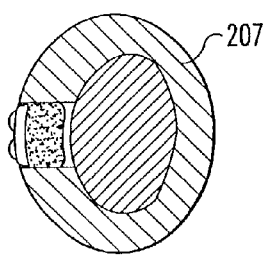 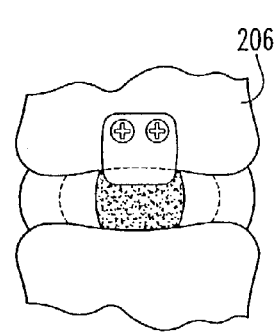
Fig. 20a   Fig. 20b   Fig. 20c
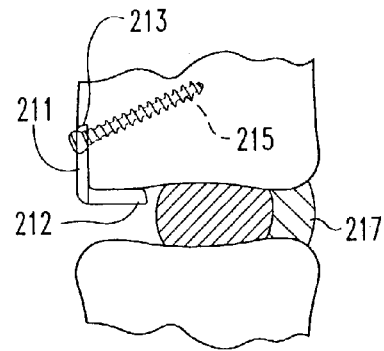 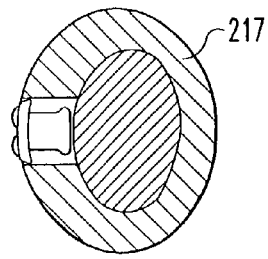 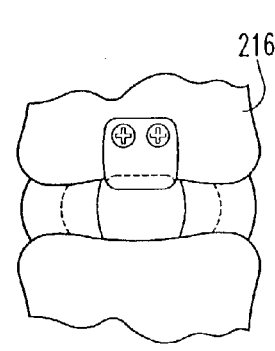
Fig. 21a   Fig. 21b   Fig. 21c

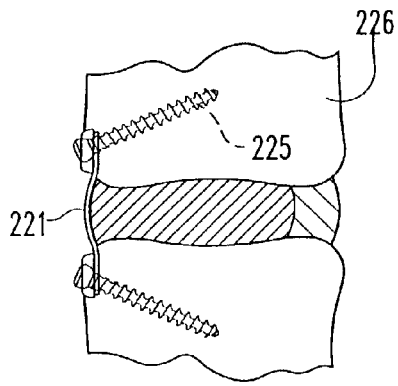 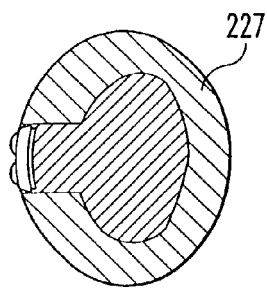 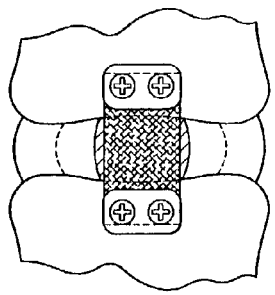
Fig. 22a  Fig. 22b  Fig. 22c
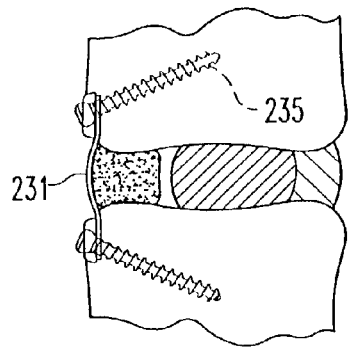 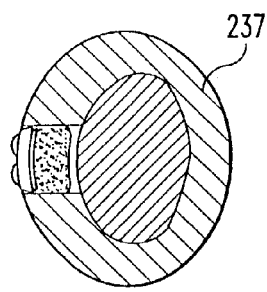 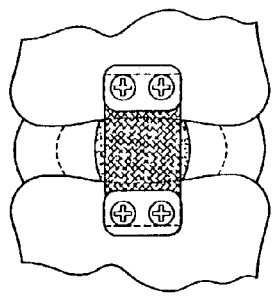
Fig. 23a  Fig. 23b  Fig. 23c
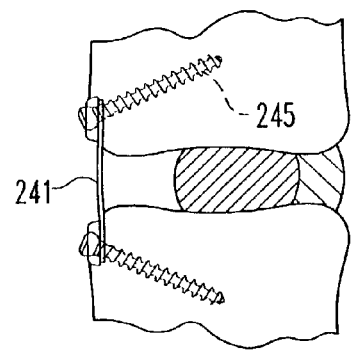 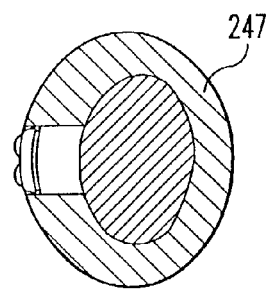 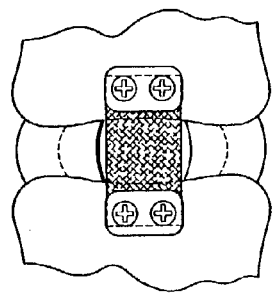
Fig. 24a  Fig. 24b  Fig. 24c

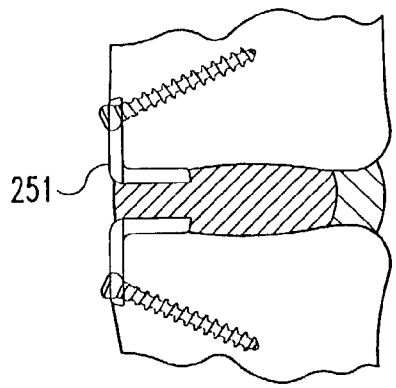 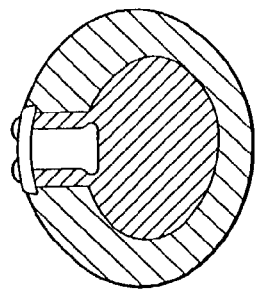
Fig. 25a  Fig. 25b
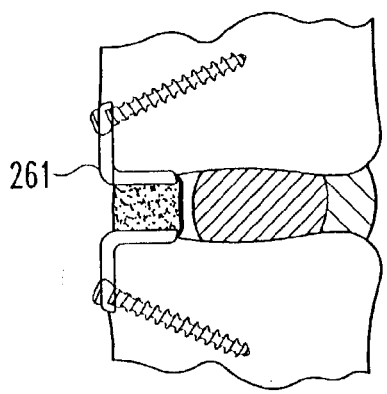 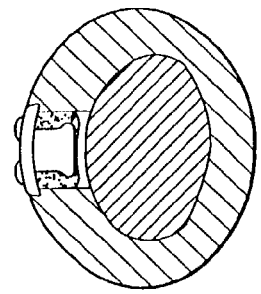
Fig. 26a  Fig. 26b
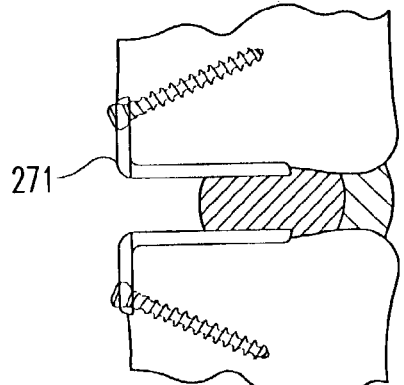 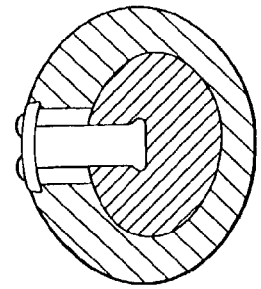
Fig. 27a  Fig. 27b

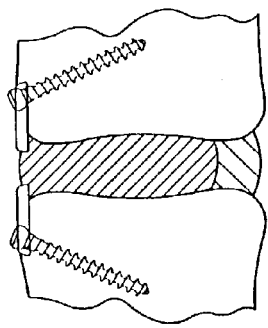 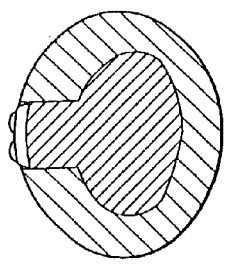 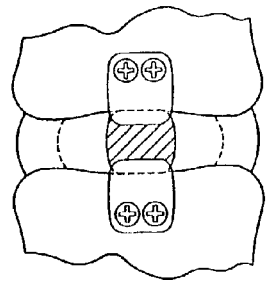
Fig. 28a  Fig. 28b  Fig. 28c
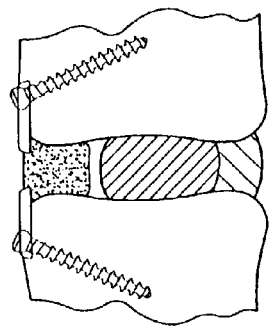 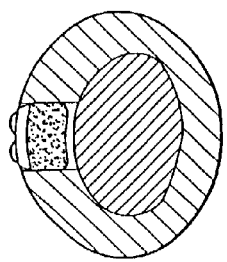 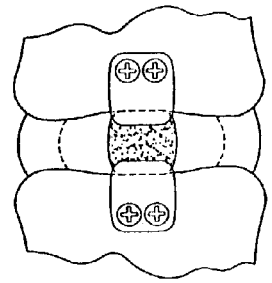
Fig. 29a  Fig. 29b  Fig. 29c
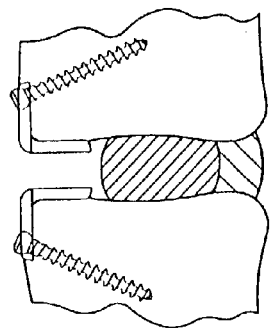 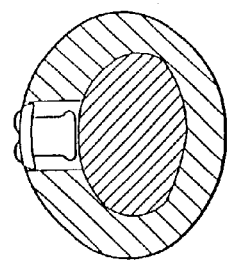 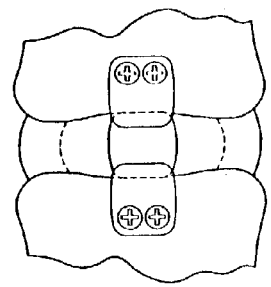
Fig. 30a  Fig. 30b  Fig. 30c

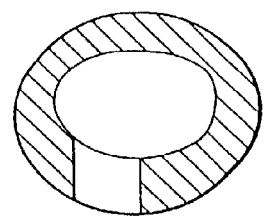 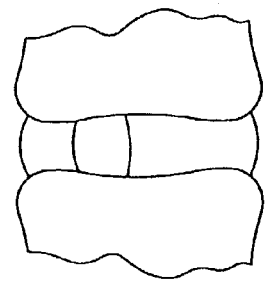
Fig. 31a    Fig. 31b
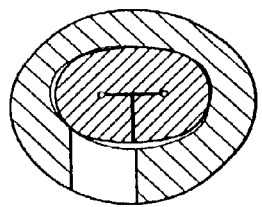 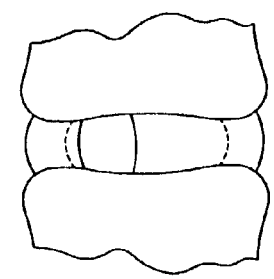
Fig. 32a    Fig. 32b
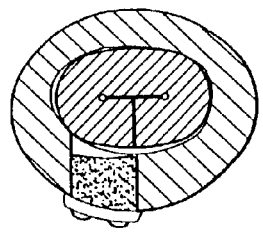 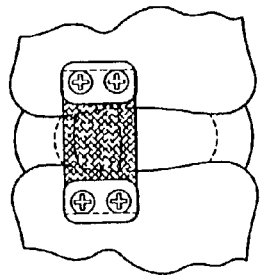
Fig. 33a    Fig. 33b
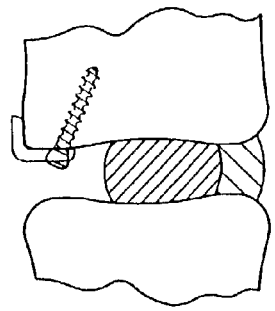 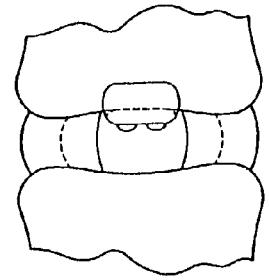
Fig. 34a    Fig. 34b

SYSTEM AND METHOD FOR BLOCKING AND/OR RETAINING A PROSTHETIC SPINAL IMPLANT

This application claims the benefit of Provisional Application No. 60/432,368, filed Dec. 10, 2002.

FIELD OF THE INVENTION

The present invention relates generally to spinal implants, and more particularly to devices for blocking and/or retaining implants in an intervertebral disc space.

BACKGROUND OF THE INVENTION

The intervertebral disc functions to stabilize the spine and to distribute forces between vertebral bodies. A normal disc includes a gelatinous nucleus pulposus, an annulus fibrosis and two vertebral end plates. The nucleus pulposus is surrounded and confined by the annulus fibrosis.

Intervertebral discs may be displaced or damaged due to trauma or disease. Disruption of the annulus fibrosis allows the nucleus pulposus to protrude into the spinal canal, a condition commonly referred to as a herniated or ruptured disc. The extruded nucleus pulposus may press on the spinal nerve, which may result in nerve damage, pain, numbness, muscle weakness and paralysis. Intervertebral discs may also deteriorate due to the normal aging process. As a disc dehydrates and hardens, the disc space height will be reduced, leading to instability of the spine, decreased mobility and pain.

One way to relieve the symptoms of these conditions is by surgical removal of a portion or all of the intervertebral disc. The removal of the damaged or unhealthy disc may allow the disc space to collapse, which could lead to instability of the spine, abnormal joint mechanics, nerve damage, as well as severe pain. Therefore, after removal of the disc, adjacent vertebrae are typically fused to preserve the disc space.

Several devices exist to fill an intervertebral space following removal of all or part of the intervertebral disc in order to prevent disc space collapse and to promote fusion of adjacent vertebrae surrounding the disc space. Even though a certain degree of success with these devices has been achieved, full motion is typically never regained after such intervertebral fusions.

Attempts to overcome these problems have led to the development of disc replacements. Many of these devices are complicated, bulky and made of a combination of metallic and elastomeric components and thus never fully return the full range of motion desired. More recently, efforts have been directed to replacing the nucleus pulposus of the disc with a similar gelatinous material, such as a hydrogel. However, once positioned in the disc space, many hydrogel implants may migrate in the disc space and/or may be expelled from the disc space through an annular defect. Closure of the annular defect, or other opening, using surgical sutures or staples following implantation is typically difficult and, in some cases, ineffective.

A need therefore exists for a nucleus pulposus or other spinal implant that resists migration from the disc space, as well as for devices and methods that block or retain the implants so that the implants are more resistant to migration and/or expulsion through an opening in the annulus fibrosis. The present invention addresses these needs.

SUMMARY OF THE INVENTION

Devices and methods for blocking and/or retaining a prosthetic spinal implant member in an intervertebral disc space are provided. In a first aspect of the invention the device comprises a first blocking member having an anchoring end and a blocking end. The anchoring end is anchored to a vertebra, and the blocking end is free and unconnected to a prosthetic spinal implant, and is positioned to block a prosthetic spinal implant from being expelled from an intervertebral disc space.

In a second embodiment the device further includes a second blocking member having an anchoring end and a blocking end. The anchoring end of the second blocking member is anchored to a vertebra, and the blocking end of the second blocking member is free and unconnected to a prosthetic spinal implant, and is positioned to block a prosthetic spinal implant from being expelled from an intervertebral disc space.

Methods for anchoring a spinal implant are also provided. In one aspect of the invention the method comprises:
(a) implanting a prosthetic spinal implant member in an intervertebral disc space;
(b) providing a first blocking member having an anchoring end and a blocking end, wherein said blocking end is free and unconnected to a prosthetic spinal implant;
(c) positioning the blocking end of said first blocking member in a position effective to block said prosthetic spinal implant from being expelled from the intervertebral disc space; and
(d) securing the anchoring end of said first blocking member to a vertebra in a manner in which the blocking end of said first blocking member is maintained in a position effective to block said prosthetic spinal implant from being expelled from the intervertebral disc space.

In another embodiment the method additionally includes the steps of:
(e) providing a second blocking member having an anchoring end and a blocking end, wherein said blocking end is free and unconnected to a prosthetic spinal implant; and
(f) positioning the blocking end of said second blocking member in a position effective to block said prosthetic spinal implant from being expelled from the intervertebral disc space; and
(g) securing the anchoring end of said second blocking member to a vertebra in a manner in which the blocking end of said second blocking member is maintained in a position effective to block said prosthetic spinal implant from being expelled from the intervertebral disc space.

In a third embodiment the method comprises:
(a) implanting a prosthetic spinal implant in an intervertebral disc space;
(b) providing a flexible blocking member having a first anchoring end, a second anchoring end, and a blocking portion, wherein said flexible blocking member is unconnected to said prosthetic spinal implant; and
(c) securing said first anchoring end to a vertebra; and
(d) securing said second anchoring end to a vertebra;
wherein said securing steps are accomplished in a manner effective to position said blocking portion in a position effective to block said prosthetic spinal implant from being expelled from the intervertebral disc space.

One object of the present invention is to provide devices for anchoring spinal implants so they will be resistant to excessive migration in, and/or expulsion from, the intervertebral disc space. Further objects and advantages of the present invention will be apparent from the following description.

BRIEF DESCRIPTION OF THE FIGURES

FIGS. 1a and 1b show one embodiment of the present invention, wherein the device includes an L-shaped plate attached to the implant, and further wherein the implant fills the annular opening.

FIGS. 2a and 2b show another embodiment of the present invention, wherein the device includes an L-shaped plate attached to an annular plug, and further wherein the annular plug fills the annular opening.

FIGS. 3a and 3b show another embodiment of the present invention, wherein the device includes an L-shaped plate attached to the implant, and further wherein there is nothing in the annulus.

FIGS. 4a–4c show another embodiment of the present invention, wherein the device includes a flat plate blocks implant, and further wherein the implant fills the annulus.

FIGS. 5a–5c show another embodiment of the present invention, wherein the device includes a flat plate blocks plug, and further wherein the plug fills the annulus.

FIGS. 6a–6c show another embodiment of the present invention, wherein the device includes an L-shaped plate not attached to the implant, and further wherein there is nothing in the annulus opening.

FIGS. 7a–7c show another embodiment of the present invention, wherein the device includes a double plate with a flexible band between, and further wherein the implant fills the annulus.

FIGS. 8a–8c show another embodiment of the present invention, wherein the device includes a double plate with a flexible band between, and further wherein there is a separate annulus plug.

FIGS. 9a–9c show another embodiment of the present invention, wherein the device includes a double plate with a flexible band between, and further wherein there is nothing in the annulus opening.

FIGS. 10a and 10b show another embodiment of the present invention, wherein the device includes double L-shaped plates attached to the implant, and further wherein the implant fills the annulus.

FIGS. 11a and 11b show another embodiment of the present invention, wherein the device includes double L-shaped plates attached to the annular plug, and further wherein the plug fills the annulus.

FIGS. 12a and 12b show another embodiment of the present invention, wherein the device includes double L-shaped plates attached to the implant, and further wherein there is nothing in the annulus opening.

FIGS. 13a–13c show another embodiment of the present invention, wherein the device includes a double flat plates block implant, and further wherein the implant fills the annulus.

FIGS. 14a–14c show another embodiment of the present invention, wherein the device includes a double flat plates block plug, and further wherein the plug fills the annulus.

FIGS. 15a–15c show another embodiment of the present invention, wherein the device includes a double flat plates not attached to the implant, and further wherein there is nothing in the annulus opening.

FIGS. 16a and 16b show another embodiment of the present invention, wherein the device includes an L-shaped plate attached to the implant, and further wherein the implant fills the annulus.

FIGS. 17a and 17b show another embodiment of the present invention, wherein the device includes an L-shaped plate attached to the annular plug, and further wherein the plug fills the annulus.

FIGS. 18a and 18b show another embodiment of the present invention, wherein the device includes an L-shaped plate attached to the implant, and further wherein there is nothing in the annulus opening.

FIGS. 19a–19c show another embodiment of the present invention, wherein the device includes a flat plate blocks implant, and further wherein the implant fills the annulus.

FIGS. 20a–20c show another embodiment of the present invention, wherein the device includes a flat plate blocks plug, and further wherein the plug fills the annulus.

FIGS. 21a–21c show another embodiment of the present invention, wherein the device includes an L-shaped plate not attached to the implant, and further wherein there is nothing in the annulus opening.

FIGS. 22a–22c show another embodiment of the present invention, wherein the device includes a double plate with a flexible band between, and further wherein the implant fills the annulus.

FIGS. 23a–23c show another embodiment of the present invention, wherein the device includes a double plate with a flexible band between, and further wherein there is a separate annulus plug.

FIGS. 24a–24c show another embodiment of the present invention, wherein the device includes a double plate with a flexible band between, and further wherein there is nothing in the annulus opening.

FIGS. 25a and 25b show another embodiment of the present invention, wherein the device includes double L-shaped plates attached to the implant, and further wherein the implant fills the annulus.

FIGS. 26a and 26b show another embodiment of the present invention, wherein the device includes double L-shaped plates attached to the annular plug, and further wherein the plug fills the annulus.

FIGS. 27a and 27b show another embodiment of the present invention, wherein the device includes double L-shaped plates attached to the implant, and further wherein there is nothing in the annulus opening.

FIGS. 28a–28c show another embodiment of the present invention, wherein the device includes a double flat plates block implant, and further wherein the implant fills the annulus.

FIGS. 29a–29c show another embodiment of the present invention, wherein the device includes a double flat plates block plug, and further wherein the plug fills the annulus.

FIGS. 30a–30c show another embodiment of the present invention, wherein the device includes a double flat plates not attached to the implant, and further wherein there is nothing in the annulus opening.

FIGS. 31 through 33 show steps in a preferred procedure for using the inventive implants.

FIG. 34 shows an embodiment of the present invention where the securing member (in this case, a screw) is attached to the vertebral end plate.

DESCRIPTION OF THE PREFERRED EMBODIMENTS

For the purposes of promoting an understanding of the principles of the invention, reference will now be made to certain preferred embodiments and specific language will be used to describe the same. It will nevertheless be understood that no limitation of the scope of the invention is thereby intended. All embodiments of the present invention, including those explicitly disclosed, those inherently disclosed, and those that would normally occur to persons skilled in the art, are desired to be protected.

The present invention relates to prosthetic spinal implants that are blocked and/or anchored to prevent excessive migration in and/or expulsion from the disc space. Methods of using such implants are also disclosed. The spinal implants described herein include those that may be useful as nucleus pulposus replacements, partial or complete disc replacements, and those that may be useful in other disc reconstruction or augmentation procedures.

Referring now to the drawings, FIGS. 1a and 1b show one preferred embodiment of the present invention. Device 10 may include a first, rigid anchoring member 11, having a first end 12 and a second end 13. A prosthetic implant member 14 is attached to, and completely covers, first end 12 of anchoring member 11. At least one securing member 15 is attached to the second end 13 of anchoring member 11. Securing member 15 is securable to a vertebra 16.

As shown in FIGS. 1a and 1b, in some embodiments of the invention implant member 14 extends into, and substantially fills, both the vacated nucleus space and opening 18 in annulus 17. The vacated nucleus space and opening 18 are both formed during the discectomy procedure that removes the degenerated disc that is replaced by implant member 14 in the illustrated embodiment.

Anchoring member 11 may be "L" shaped as shown in FIG. 1a, or it may be another shape effective to position the prosthetic implant member 14 in a desired location when one end of the anchoring member is secured to a vertebra. Anchoring member 11 is preferably made of a rigid, biocompatible material, such as metals, ceramics, composites, etc. For example, carbon fiber reinforced composites such as carbon fiber/epoxy composites or carbon fiber/polyaryletherketone composites may be used, as may a wide variety of metallic materials, such as, for example, shape memory materials, stainless steel, titanium, titanium alloys, cobalt chrome alloys, and combinations thereof.

As shown in FIGS. 2a and 2b, in other embodiments of the present invention implant member 24 may extend into, and/or substantially fill, only opening 28 of annulus 27. In this embodiment the nucleus space is filled with a separate prosthetic disc nucleus 29.

As shown in FIGS. 3a and 3b, in other embodiments implant member 34 may extend into, and/or substantially fill, only the vacated nucleus space, leaving opening 38 of annulus 37 unplugged.

As shown in FIGS. 4a–4c, alternative embodiments of the present invention comprise a rigid anchoring member that blocks, but is not attached to, a prosthetic spinal implant member. As with the prior embodiments, rigid anchoring member 41 may have a first end 42 and a second end 43. At least one securing member 45 may be attached to the second end 43 of anchoring member 41, but the first end 42 is left free and unconnected to prosthetic spinal implant 44. Securing member 45 may be secured to a vertebra 46.

FIGS. 5a–5c show another embodiment where a rigid anchoring member blocks, but is not attached to, a prosthetic spinal implant member. In this embodiment rigid anchoring member 51 has a first end 52 and a second end 53, with at least one securing member 55 being attached to second end 53. Here too, first end 52 is left free and unconnected to prosthetic spinal implant 54, and securing member 55 may be secured to a vertebra 56.

In the embodiment shown in FIGS. 5a–5c, rigid anchoring member 51 blocks an implant 54 which is separate and distinct from prosthetic nucleus 59. This is in contrast to the embodiment shown in FIGS. 4a–4c, where rigid anchoring member 41 blocks a single prosthetic nucleus implant 44. As with the embodiment shown in FIGS. 1a–1b, the single prosthetic implant 44 of FIGS. 4a–4c extends into, and substantially fills, both the vacated nucleus space and opening 48 in annulus 47.

FIGS. 6a–6c show a further embodiment of the present invention, corresponding to the embodiment shown in FIGS. 3a–3b but with a rigid anchoring member that blocks, but is not attached to, a prosthetic spinal implant member. In this embodiment rigid anchoring member 61 has a first end 62 and a second end 63, with at least one securing member 65 being attached to second end 63. As with the embodiments shown in FIGS. 4 and 5, first end 62 is left free and unconnected to prosthetic spinal implant 64, and securing member 65 may be secured to a vertebra.

The anchoring member of the device may also, in other forms of the invention, include a flexible implant-blocking material. For example, FIGS. 7a–7c show one embodiment wherein anchoring member 70 comprises a flexible band 71 anchored at each end by one or more securing members 75. In the embodiment shown in FIGS. 7a–7c, anchoring member 70 retains implant 74 to keep the implant from being expelled from the intervertebral disc space. Implant 74 extends into, and substantially fills, both the vacated nucleus space and opening 78 in annulus 77.

FIGS. 8a–8c show a related embodiment where flexible band 81 blocks both an annular plug 84, and a prosthetic nucleus 89. Flexible band 81 is anchored at each end by one or more securing members 85, in a manner similar to that used in the preceding embodiment.

FIGS. 9a–9c show an embodiment where flexible band 91 blocks a prosthetic nucleus 99, leaving the annular opening 98 substantially implant-free. Flexible band 91 is anchored at each end by one or more securing members 95, which are secured to vertebra 96 as previously described.

FIGS. 10a–10b through 15a–15c show embodiments similar to those shown in FIGS. 1a–1b through 6a–6c, but with a second anchoring member being used and attached to the corresponding vertebra. Accordingly, FIGS. 10a–10b show a device 100 that includes a two, rigid anchoring members 101a and 101b, each of said anchoring members having a first end 102a and 102b respectively, that completely covers second ends 103a and 103b. A prosthetic implant member 104 is attached to, and completely covers, first ends 102a and 102b of anchoring members 101a and 101b. At least one securing member (e.g., 105a and 105b) is attached to the second end (e.g., 103a and 103b) of each anchoring member. The securing members are securable to a vertebra.

Implant member 104 extends into, and substantially fills, both the vacated nucleus space and opening 108 in annulus 107. In the embodiment shown in FIGS. 11a–1b, the implant member 114 fills only the annular opening, and a second, separate prosthetic nucleus 119 is used.

As shown in FIGS. 12a and 12b, in other embodiments implant members 124a and 124b may extend into, and/or substantially fill, only the vacated nucleus space, leaving opening 128 of annulus 127 unplugged.

As shown in FIGS. 13a–13c, alternative embodiments of the present invention comprise a rigid anchoring member that blocks, but is not attached to, a prosthetic spinal implant member. As with the prior embodiments, each rigid anchoring member 131a and 131b may have a first end 132a and 132b and a second end 133a and 133b. At least one securing member 135 may be attached to the second end 133 of each anchoring member 131, but the first end 132 is left free and unconnected to prosthetic spinal implant 134. Securing member 135 may be secured to a vertebra 136.

FIGS. 14a–14c show another embodiment where a rigid anchoring member blocks, but is not attached to, a prosthetic spinal implant member. In this embodiment each rigid anchoring member 141a and 141b has a first end 142 and a second end 143, with at least one securing member 145 being attached to second end 143. Here too, first end 142 is left free and unconnected to prosthetic spinal implant 144, and securing member 145 may be secured to a vertebra 146.

In the embodiment shown in FIGS. 14a–14c, rigid anchoring member 141 blocks an implant 144 which is separate and distinct from prosthetic nucleus 149. This is in contrast to the embodiment shown in FIGS. 13a–13c, where rigid anchoring member 131 blocks a single prosthetic nucleus implant 134. As with the embodiment shown in FIGS. 1a–1b and FIGS. 10a–10b, the single prosthetic implant 134 of FIGS. 13a–13c extends into, and substantially fills, both the vacated nucleus space and opening 138 in annulus 137.

FIGS. 15a–15c show a further embodiment of the present invention, corresponding to the embodiment shown in FIGS. 12a–12b but with a rigid anchoring member that blocks, but is not attached to, a prosthetic spinal implant member. In this embodiment rigid anchoring member 151 has a first end 152 and a second end 153, with at least one securing member 155 being attached to second end 153. As with the embodiments shown in FIGS. 4 and 5 and FIGS. 11a–11b, first end 152 is left free and unconnected to prosthetic spinal implant 154, and securing member 155 may be secured to a vertebra.

Blocking and/or retaining members such as those shown in FIGS. 1–15 may be secured to a vertebra as shown, or they may be "flush fit" as shown in FIGS. 16a–16b through 30a–30c. In the flush fit embodiments, bone is cut away from the vertebra so that the anchoring/blocking member may be attached in a manner in which the outside surface of the anchoring/blocking member is substantially flush with the outer surface of the vertebra.

When an "L-shaped" anchoring/blocking member is used, the anchoring/blocking member is preferably mounted to contact the vertebral end plate, as shown in FIGS. 16a–16b through 18a–18b, FIGS. 21a–21c, FIGS. 25a–25b through 27a–27b, and in FIGS. 30a–30c. It is preferred that the lower portion of the anchoring/blocking member extend into the intervertebral space to effectively block the natural or prosthetic disc. When a prosthetic disc or annular plug is being blocked or retained, an adhesive may be used to secure the prosthetic disc or plug to the anchoring/blocking member. In such cases the need for extension into the intervertebral space is reduced or eliminated.

It is also to be appreciated that in "flush fit" embodiments using an "L-shaped" anchoring member, the end connected to the implant need not be covered completely by the implant. Accordingly, the embodiment shown in FIGS. 16a–16b differs from the embodiment shown in FIGS. 1a–1b in that the first end 162 of anchoring member 161 is not completely covered by implant 164.

Similarly, in FIGS. 17a–17b, first end 172 of anchoring member 171 is not completely covered by implant 174 as was the case in the embodiment shown in FIGS. 2a–2b. In the same manner, first end 182 of anchoring member 181 is not completely covered by implant 184 as was the case in the embodiment shown in FIGS. 3a–3b.

In the "double anchor" embodiments of FIGS. 25a–25b through 27a–27b the distal ends of the implants need not be completely covered by the corresponding implant. Accordingly, none of anchoring member ends 252, 262, and 272 are completely covered by implants 254, 264, and 274, respectively, as were anchoring member ends 102, 112, and 122.

As to methods of using the disclosed anchored implants, the procedure typically begins with a discectomy to remove the degenerated natural disc. An opening is provided in the annulus, and the degenerated disc material is removed. A prosthetic nucleus in delivered into the disc space, and the anchoring and/or blocking member(s) are installed and attached.

As to the materials that may be used to make the various components of the preferred embodiments, anchoring/blocking members may be formed from rigid, semi-rigid, or flexible biocompatible materials including metals, polymers, ceramics, composites, natural or synthetic bone materials, etc. For example, carbon fiber reinforced composites such as carbon fiber/epoxy composites or carbon fiber/polyaryletherketone composites may be used, as may a wide variety of metallic materials, such as, for example, stainless steel, titanium, titanium alloys, cobalt chrome alloys, tantalum, shape memory alloys, etc.

Examples of appropriate polymeric materials include, but are not limited to, synthetic polymers such as polyurethanes, silicones, polyolefins, polyvinylalcohols, polyesters, polyacrylonitriles, polyetherketones, polycarbonates, polymethacrylates, polyamides, etc. In other embodiments natural polymers, such as cellulose, may be used.

Specific preferred polymers include polytetrafluoroethylene, polymethylmethacrylate, polymethyletherketone, polyacrylamide, polyparaphenylene terephthalamide, polyethylene, polystyrene, polypropylene, and combinations of these materials. In some embodiments the polymeric materials are braided in the form of a cord, cable, or may have some other appropriate configuration, and combinations thereof.

Examples of ceramic materials that may be used for the various components of the present invention include alumina, zirconia, alumina-zirconia composites, pyrolytic carbon, and polycrystalline diamond compact materials.

A wide variety of spinal implants for serving differing functions may be anchored or blocked with the anchoring/blocking devices described herein, including implants sized and configured for nucleus pulposus replacements, implants sized and configured for partial or full disc replacements, or other implants designed for other disc reconstruction or augmentation purposes, such as a fusion cage. Elastic, or otherwise resilient, implants are most preferred. For example, implants may be formed from hydrophilic materials, such as hydrogels, or may be formed from biocompatible elastomeric materials known in the art, including silicone, polyurethane, polyolefins such as polyisobutylene and polyisoprene, copolymers of silicone and polyurethane, neoprene, nitrile, vulcanized rubber and combinations thereof. In a preferred embodiment, the vulcanized rubber is produced by a vulcanization process utilizing a copolymer produced, for example, as in U.S. Pat. No. 5,245,098 to Summers et al., from 1-hexene and 5-methyl-1,4-hexadiene. Preferred hydrophilic materials are hydrogels. Suitable hydrogels include natural hydrogels, and those formed from polyvinyl alcohol, acrylamides such as polyacrylic acid and poly (acrylonitrile-acrylic acid), polyurethanes, polyethylene glycol, poly(N-vinyl-2-pyrrolidone), acrylates such as poly(2-hydroxy ethyl methacrylate) and copolymers of acrylates with N-vinyl pyrolidone, N-vinyl lactams, acrylamide, polyurethanes and polyacrylonitrile or may be formed from other similar materials that form a hydrogel. The hydrogel materials may further be cross-linked to provide further strength to the implant. Examples of different types of polyurethanes include thermoplastic or thermoset polyurethanes, aliphatic or aromatic polyurethanes, polyetherurethane, polycarbonate-urethane and silicone polyether-urethane. Other suitable hydrophilic polymers include naturally-occurring materials such as glucomannan gel, hyaluronic acid, polysaccharides, such as cross-linked carboxyl-containing polysaccharides, and combinations thereof. The nature of the materials employed to form the elastic body should be selected so the formed implants have sufficient load bearing capacity. In preferred embodiments, a compressive strength of at least about 0.1 MPa is desired, although compressive strengths in the range of about 1 MPa to about 20 MPa are more preferred.

It is to be appreciated that natural materials may be used to make the prosthetic implants disclosed in the present invention. For example, natural collagen material such as allogenic or xenogenic disc nucleus material may be used. Alternatively, collagen-based material derived from natural, collagen-rich tissue, such as intervertebral disc, fascia, ligament, tendon, demineralized bone matrix, etc., may be used. The material may be autogenic, allogenic, or xenogenic, or it may be of human-recombinant origin. In alternative embodiments the collagen-based material may be a synthetic, collagen-based material. Examples of preferred collagen-rich tissues include disc annulus, fascia lata, planar fascia, anterior or posterior cruciate ligaments, patella tendon, hamstring tendons, quadriceps tendons, Achilles tendons, skins, and other connective tissues.

In some embodiments the implant material is an inelastic, semi-rigid material. Such materials stretch very little, if at all, but allow some compression. The compression typically occurs when air in the implant is pushed out, such as when a small roll of fabric is compressed.

The implants can be shaped as desired. For example, the nucleus pulposus implants may take the form of a cylinder, a rectangle, or other polygonal shape or may be substantially oval.

The securing and/or blocking members may be made of any appropriate biocompatible material, such metals, ceramics, polymers and combinations thereof. Non-resorbable metallic materials include biocompatible stainless steel, titanium, titanium alloys, titanium-vanadium-aluminum alloy, cobalt alloys such as cobalt-chromium alloy, cobalt-chromium-molybdenum alloy, and cobalt-nickel-chromium-molybdenum alloy, tantalum, niobium, hafnium, tungsten, shape memory materials as described above, especially those exhibiting superelastic behavior and including metals, and alloys thereof. Resorbable materials include polylactide, polyglycolide, tyrosine-derived polycarbonate, polyanhydride, polyorthoester, polyphosphazene, bioactive glass, calcium phosphate, such as hydroxyapatite, and combinations thereof.

The anchoring devices may also be anchored with other soft tissue anchors known in the art, including suture anchors commonly used in arthroscopy or sports medicine surgeries, for example. In the case of a soft tissue or suture anchor, the end of the elongated body of the anchoring device is attached to the end of the anchor, which is embedded and anchored in an adjacent vertebral body.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A method for retaining a prosthetic spinal implant in an intervertebral disc space, said method comprising:
    (a) implanting a prosthetic spinal implant member in an intervertebral disc space;
    (b) providing a first L-shaped blocking member having an anchoring end and a blocking end, wherein said blocking end is free and unconnected to a prosthetic spinal implant; and
    (c) positioning the blocking end of said first L-shaped blocking member in an intervertebral disc space in a position effective to block said prosthetic spinal implant from being expelled from the intervertebral disc space; and
    (d) securing the anchoring end of said first L-shaped blocking member to a vertebra in a manner in which the blocking end of said first L-shaped blocking member is maintained in a position effective to block said prosthetic spinal implant from being expelled from the intervertebral disc space.

2. The method of claim 1 wherein said prosthetic implant member comprises a prosthetic nucleus.

3. The method of claim 1 wherein said prosthetic implant member comprises consists essentially of a prosthetic nucleus.

4. The method of claim 1 wherein said prosthetic implant member comprises a material selected from the group consisting of metals, polymers, ceramics, composites, natural collagen-source materials, and synthetic collagen-type materials, and combinations thereof.

5. The method of claim 1, wherein said prosthetic implant member comprises a flexible elastic body.

6. The method of claim 5, wherein said prosthetic implant member comprises a polymeric material.

7. The method of claim 6, wherein said polymeric material comprises a material selected from the group consisting of polyurethane, silicones, polyaryletherketones, polyarylacrylates, polyacrylamideacrylates, polyolefins, polyvinyl alcohols, polyacrylonitriles, polyesters.

8. The method of claim 5, wherein said prosthetic implant member comprises a natural, collagen-source material.

9. The method of claim 8, wherein said natural, collagen-source material comprises a material selected from the group consisting of: disc annulus material, fascia lata material, planar fascia material, anterior or posterior cruciate ligament material, patella tendons, hamstring tendons, quadriceps tendons, Achilles tendons, skins, and connective tissues.

10. The method of claim 5, wherein said prosthetic implant member comprises a synthetic, collagen-type material.

11. The method of claim 1, wherein said prosthetic implant member comprises an inelastic, semi-rigid material.

12. The method of claim 1, wherein said prosthetic implant member comprises a rigid articulating body.

13. The method of claim 12, wherein said rigid articulating body comprises a polymeric material.

14. The method of claim 13, wherein said polymeric material comprises a material selected from the group consisting of polyurethane, silicones, polyolefins, polyvinyl alcohols, polyacrylonitriles, polyesters.

15. The method of claim 12, wherein said rigid articulating body comprises a metal.

16. The method of claim 15, wherein said metal comprises a material selected from the group consisting of stainless steels, cobalt chrome alloys, titanium, titanium alloys, tantalum, and shape memory metals.

17. The method of claim 12, wherein said rigid articulating body comprises a ceramic.

18. The method of claim 17, wherein said ceramic comprises a material selected from the group consisting of alumina, zirconia, alumina-zirconia composites, pyrolytic carbon, and polycrystalline diamond compact materials.

19. The method of claim 1, wherein said anchoring end of said first L-shaped blocking member is secured to a vertebra with a bone screw or a soft tissue anchor.

* * * * *